United States Patent
Aktogu et al.

Patent Number: 4,886,802
Date of Patent: Dec. 12, 1989

[54] 17-AZA-20,21, DINOREBURNAMENINES

[75] Inventors: Nurgün Aktogu, Robinson; Francois Clemence, Paris, both of France

[73] Assignee: Roussel Uclaf, Paris, France

[21] Appl. No.: 181,657

[22] Filed: Apr. 14, 1988

[30] Foreign Application Priority Data

Apr. 15, 1987 [FR] France ................................ 87 05361

[51] Int. Cl.⁴ .................. C07D 487/22; C07D 487/14; C07D 403/06; A61K 31/495
[52] U.S. Cl. .................................... 514/250; 544/342; 544/343; 544/373; 548/505; 548/507
[58] Field of Search ........................ 544/342; 514/250

[56] References Cited

U.S. PATENT DOCUMENTS 3,843,653 10/1974 Aldridge .............................. 544/342

Primary Examiner—Mark L. Berch
Attorney, Agent, or Firm—Bierman and Muserlian

[57] ABSTRACT

A compound selected from the group consisting of all possible isomeric forms, optically active isomers and racemic mixtures of compounds of the formula

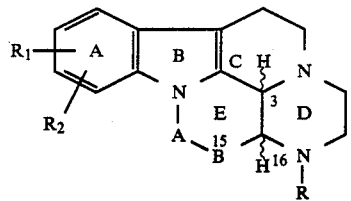

wherein $R_1$ and $R_2$ are individually selected from the group consisting of hydrogen, halogen, alkyl and alkoxy of 1 to 5 carbon atoms, —OH, —CF$_3$ and —NO$_2$, R is selected from the group consisting of hydrogen, alkyl of 1 to 5 carbon atoms, aralkyl of 7 to 12 carbon atoms, benzoyl and acyl of an alkanoic acid of 1 to 12 alkyl carbon atoms and

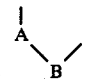

is selected from the group consisting of

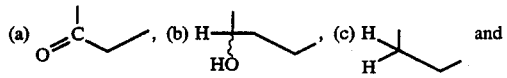

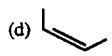

and their non-toxic, pharmaceutically acceptable acid addition salts having analgesic activity as well as cerebral oxygenating and vaso regulating activity.

15 Claims, No Drawings

17-AZA-20,21, DINOREBURNAMENINES

STATE OF THE ART

Related application is commonly assigned French Patent No. 2 168 853 as well as chem. Abst. Vol. 81 (1974) p 498 No. 105 181 k

OBJECTS OF THE INVENTION

It is an object of the invention to provide the novel compounds of formula I and their non-toxic, pharmaceutically acceptable acid addition salts and a novel process and novel intermediates for their preparation.

It is another object of the invention to provide novel analgesic compositions and a novel method of relieving pain in warm-blooded animals.

These and other objects and advantages of the invention will become obvious from the following detailed description.

THE INVENTION

The novel compounds of the invention are compounds selected from the group consisting of all possible isomeric forms, optically active isomers and racemic mixtures of compounds of the formula

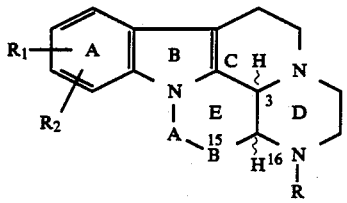

I wherein $R_1$ and $R_2$ are individually selected from the group consisting of hydrogen, halogen, alkyl and alkoxy of 1 to 5 carbon atoms, —OH, —$CF_3$ and —$NO_2$, R is selected from the group consisting of hydrogen, alkyl of 1 to 5 carbon atoms, aralkyl of 7 to 12 carbon atoms, benzoyl and acyl of an alkanoic acid of 1 to 12 alkyl carbon atoms and

is selected from the group consisting of

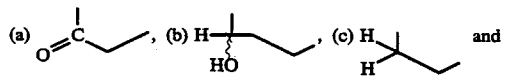

and

and their non-toxic, pharmaceutically acceptable acid addition salts.

The hydrogen atoms in the 3- and 16-positions can have any orientation which determines if the compounds are trans or cis diastereoisomers. The 14-hydroxyl may be in the α- or β form.

Examples of $R_1$, $R_2$ and R as alkyl are n-butyl, isobutyl, pentyl and preferably methyl, ethyl, n-propyl and isopropyl. Examples of alkoxy for $R_1$ and $R_2$ are n-propoxy, isopropoxy and linear and branched butoxy, and preferably methoxy and ethoxy.

Examples of halogens for $R_1$ and $R_2$ are fluorine, bromine, iodine and preferably chlorine.

Examples of arylalkyl of 7 to 12 carbon atoms for R are benzyl and phenethyl and when R is alkylcarbonyl, it is preferably acetyl or lauroyl.

Among the preferred compounds of Formula I are those wherein $R_1$ and $R_2$ are individually selected from the group consisting of hydrogen, methyl, ethyl, methoxy, ethoxy, chlorine, —OH, —$CF_3$ and —$NO_2$, those wherein R is selected from the group consisting of hydrogen, methyl, ethyl, propyl, benzyl, phenethyl and benzoyl in all their possible isomeric forms, racemic or optical isomers and their non-toxic, pharmaceutically acceptable acid addition salts.

Among the more preferred compounds of Formula I are those wherein $R_2$ is hydrogen, those wherein $R_1$ is hydrogen, methoxy, ethoxy or chlorine, those wherein the 3- and 16-hydrogen atoms are in the trans form in all their possible isomeric forms, racemic or optically active forms and their non-toxic, pharmaceutically acceptable acid addition salts.

Specific preferred compounds of the invention are (16α) (±) 17-methyl-17-aza-20,21-dinoreburnamenin-14-(15H)-one, (16α) (±) 17-propyl-17-aza-20,21-dinoreburnamenin-14-(15H)-one, (16α) (±) 17-aza-20,21-dinoreburnamenine, (16α) (±) 14,15-dihydro-17-methyl-17-aza-20,21-dinoreburnamenine and their non-toxic, pharmaceutically acceptable acid addition salts.

Examples of suitable acids for the formation of the non-toxic, pharmaceutically acceptable acid addition salts are inorganic acids such as hydrochloric acid, hydrobromic acid, hydriodic acid, nitric acid, sulfuric acid, phosporic acid, and organic acids such as propionic acid, acetic acid, formic acid, benzoic acid, maleic acid fumaric acid, succinic acid, tartaric acid, citric acid, oxalic acid, glyoxylic acid, asparatic acid, ascorbic acid, alkylmonosulfonic acid such as methanesulfonic acid, ethanesulfonic acid, propanesulfonic acid, alkyldisulfonic acid such as methane disulfonic acid, α-, β-ethanedisulfonic acid, arylmonosulfonic acids such as benzenesulfonic acid and aryldisulfonic acid.

The novel process of the invention for the preparation of the compounds of Formula I comprises reacting a compound of the formula

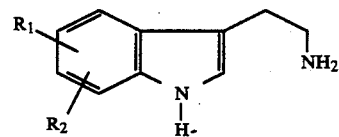

II wherein $R_1$ and $R_2$ have the significances above, with chloroacetonitrile to obtain a compound of the formula

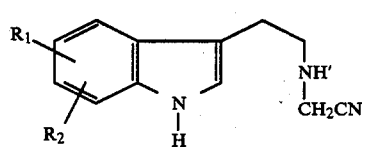

III reducing the latter to obtain a compound of the formula

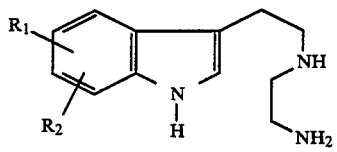

IV condensing the latter with an alkyl maleate or fumarate of the formula

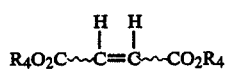

$R_4$ is an alkyl of 1 to 4 carbon atoms to obtain a compound of the formula

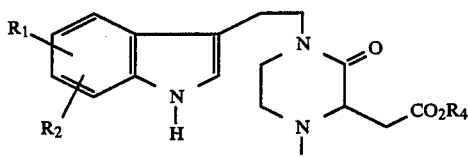

V reacting the latter with a reagent capable of introducing R', R' being R other than hydrogen to obtain a compound of the formula

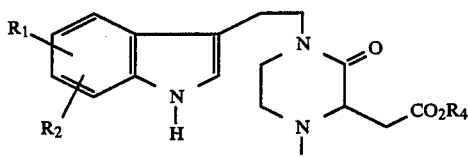

VI reacting the latter with a cyclization agent to obtain a compound of the formula

[structure] VII wherein $R_1$, $R_2$, $R_4$ and R' have the above significances and An is an anion of a strong acid, and either reducing the latter compound to obtain a compound of Formula VIII in which the 3- and 16-hydrogen atoms are in cis position

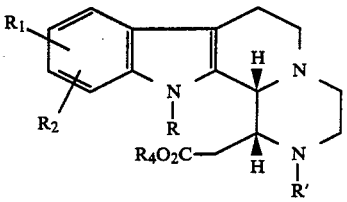

VIII optionally eliminating the R' group when the latter is benzoyl or alkylcarbonyl and cyclizing the latter to obtain a compound of the formula $I_{A1b}$ corresponding to a product of Formula I in which:

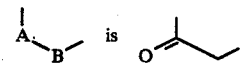

the 3- and 16-hydrogen atoms are in cis position and R is hydrogen and optionally reacting the compound of Formula $I_{A1b}$ with a reagent capable of introducing R', R' being R other than hydrogen to obtain a compound of Formula $I_{A1C}$ in which R is R' or cyclizes the compound of Formula VII to obtain a compound of the formula

[structure] IX reducing the latter to obtain a compound of Formula $I_{A2a}$ corresponding to the product of Formula I in which:

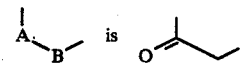

the 3- and 16-hydrogen atoms are in trans position and R is R', the R' being optionally eliminated when the latter is benzoyl or alkylcarbonyl to obtain a compound of the formula $I_{A2b}$ in which R is hydrogen, optionally reacting the latter with a reagent capable of introducing R', R' being R other than hydrogen to obtain a compound of the Formula $I_{A2c}$, optionally reducing compounds of formulae $I_{A1b}$, $I_{A1c}$, $I_{A2a}$, $I_{A2b}$, and $I_{A2c}$ into the corresponding compounds of Formulae $I_{B1b}$, $I_{B1c}$, $I_{B2a}$, $I_{B2b}$ and $I_{B2c}$ representing the compounds of Formula I in which

[structure]

the said compound of Formulae $I_{B1b}$, $I_{B1c}$, $I_{b2a}$, $I_{B2b}$ and $I_{B2c}$ optionally being reacted with a dehydrating agent to obtain the corresponding compounds of Formulae $I_{C1b}$, $I_{C1c}$, $I_{C2a}$, $I_{C2b}$ and $I_{C2c}$ representing the compounds of Formula I in which

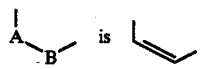

the said compounds of Formulae $I_{C1b}$, $I_{C1c}$, $I_{C2a}$, $I_{C2b}$ and $I_{C2c}$ optionally reacted with a reducing agent to obtain the corresponding compounds of Formulae $I_{D1b}$, $I_{D1c}$, $I_{D2a}$, $I_{D2b}$ and $I_{D2c}$ representing the compounds of Formula I in which:

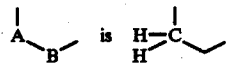

and if desired, all products of Formula I are treated with a mineral or organic acid to form the acid addition salts.

In a preferred process of the invention, the compound of Formula II is condensed with chloroacetonitrile in a basic medium to obtain a compound of Formula III.

The base used is preferably potassium carbonate, either in the presence of tetrabutylammonium hydrogensulfate, or in an aprotic solvent such as dimethylformamide. Triethylamine in tetrahydrofuran may also be used. The reduction to obtain the compound of Formula IV is catalytic hydrogenation in the presence of Raney nickel.

The compound of formula IV is condensed with diethylmaleate in ethanol at reflux and the reagent capable of introducing R' into the compounds of formula V, $I_{A1b}$ or $I_{A2b}$ is either a formaldehyde/acetic acid mixture, if it is desired to obtain a compound of formula VI, $I_{A1c}$ or $I_{A2c}$ in which R' is methyl; or a compound of the formula X—R' in which X is halogen and R' has the above significance for R other than hydrogen. Thus, X is preferably iodine when R' is alkyl and then the operation is carried out preferably in the presence of potassium carbonate and tetrabutylammonium hydrogensulfate, chlorine when R' is benzoyl or alkylcarbonyl and bromine when R' is aralkyl. The reaction is done, for example, in the presence of a nitrogenated base such as triethylamine or a mineral base such as an alkali metal carbonate in an organic solvent such as tetrahydrofuran or dimethylformamide. When a poorly reactive or encumbered halide is used, it may be useful to operate in the presence of a sodium salt such as the iodide.

In very preferential conditions, methylation of the compound of formula $I_{A2b}$ is carried out with methyl iodide in the presence of potassium carbonate and tetrabutylammonium hydrogenosulfate or with a formic acid/formaldehyde mixture, while the methylation of the compound of formula $I_{A1b}$ is carried out with a formic acid/formaldehyde mixture.

Cyclization of the compound of formula VI into a compound of formula VII is carried out by the action of phosphorus oxychloride then of hydriodic acid or perchloric acid, the anion $An^-$ being in this case the residue of this acid. The reduction of the compound of formula VII into a compound of formula VIII is carried out with sodium borohydride. The possible elimination of R' of the compound of formula VIII and the cyclization of this compound are carried out simultaneously in an acid medium and preferably in the presence of hydrochloric acid. The cyclization of the compound of formula VII into a compound of formula IX is carried out in a basic medium and preferably an ammonia medium.

The reduction of the compound of formula IX into a compound of formula $I_{A2a}$ is carried out with sodium borohydride in the presence of acetic acid. The possible elimination of R' of the compounds of formula $I_{A2a}$ is carried out for example with an acid such as hydrochloric acid. The reduction of the compounds of formula $I_A$ in which:

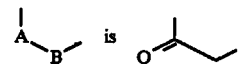

into compounds of formula $I_B$ in which

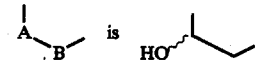

is carried out with a hydride, particularly a mixed hydride such as the mixed hydride of lithium and aluminium the diethylhydride of sodium and aluminium. The dehydration agent used to obtain from compounds of formula $I_B$ in which

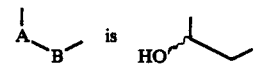

compounds of formula $I_C$ in which:

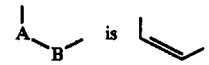

is an acid such as hydrochloric acid, hydrobromic acid, sulfuric acid, acetic acid, p-toluene sulfonic acid or methanesulfonic acid.

The reducing agent to which the compounds of formula $I_C$ in which:

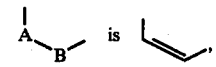

are reacted to obtain the compounds of formula $I_D$ in which

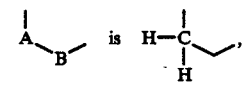

is hydrogen in the presence of a catalyst such as platinum or palladium.

The optically active forms of the products of formula I can be prepared by resolution of the racemic forms according to the usual methods.

The analgesic compositions of the invention are comprised of an analgesically effective amount of at least one compound of formula I and their non-toxic, pharmaceutically acceptable acid addition salts and an inert pharmaceutical carrier or excipient. The compositions are in the form of tablets, dragees, gelules, granules, suppositories, injectable solutions, or suspensions, ointments, creams, gels and aerosol preparations prepared in the known manner.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing and emulsifying agents and preservatives.

The compositions of the invention have a very good analgesic activity and are also useful cerebral oxygenators and vasoregulators. They are useful in the treatment of muscular, articular or nervous pains, toothaches, migraines, shingles and also as an additional treatment in infectious and feverish conditions. They are also useful in the treatment of cerebral vasculopathies and of all syndromes brought on by a deterioration in cerebral circulation.

The novel method of the invention for relieving pain in warm-blooded animals, including humans, comprises administering to warm-blooded animals an analgesically effective amount of at least one compound of formula I and their non-toxic, pharmaceutically acceptable acid addition salts. The compounds may be administered orally, rectally, parenterally or topically on skin or mucosae. The usual daily dose is depending upon the condition treated, the specific compound and the method of administration. It can be 0,25 TO 25mg/kg with a compound administered orally in adult.

Another object of the invention are the novel intermediates of the formulae III, IV, V, VI, VII, VIII and IX.

In the following examples there are described several preferred embodiments to illustrate the invention. However, it should be understood that the invention is not intended to be limited to the specific embodiments.

EXAMPLE 1

(±) 20,21-dinor-17-aza-eburnamenin-14(15H)-one dihydrochloride STEP A:
[[2-(1H-indol-3-yl)-ethyl]-amino]-acetonitrile 5 ml of water, 0.856 g of potassium carbonate, 0.210 g of n-tetrabutylammonium sulfate and 0.44 ml of acetonitrile chloride were added to a suspension of 1 g of tryptamine in 10 ml of dichloromethane and the mixture was stirred for 48 hours under an inert atmosphere at ambient temperature. Then, the mixture was decanted and the organic phase was washed with water and dried. The solvent was evaporated and the residue was chromatographed on silica. Elution with a mixture of methylene chloride and ethyl acetate (7-3) yielded 0.861 g of the expected product.

| IR Spectrum (CHCl$_3$): | |
|---|---|
| NH indole | 3,480 cm$^{-1}$ |
| other NH | 3,327 cm$^{-1}$ |
| CN ~ | 2,240 cm$^{-1}$ |
|  | 2,225 cm$^{-1}$ |
| Aromatic conjugated system | 1,618 cm$^{-1}$ |
|  | 1,596 cm$^{-1}$ |
|  | 1,552 cm$^{-1}$ |

STEP B: 2-(1H-indol-3-yl)-ethylethane diamine

A solution of 5 g of the product of Step A in 100 ml of methanol was hydrogenated in the presence of 15 g of Raney nickel for 90 minutes at ambient temperature. Filtration was carried out and the filtrate was concentrated to dryness. The residue was taken up in methylene chloride, dried and brought to dryness. The resin obtained was triturated with pentane several times to obtain 4.95 g of the expected product in the form of a base.

STEP C: Ethyl 4-[2-(1H-indol-3-yl)-ethyl]-3-oxo-2-piperazine acetate 36 g of the product of Step B in 250 ml of ethanol were refluxed and 47 ml of diethyl maleate in 50 ml of ethanol were introduced hot over 5 hours 30 minutes. Reflux was maintained for a further hour and then the mixture was evaporated to dryness. The oily residue was chromatographed under pressure on silica and eluted with an ethyl acetate-ethanol mixture (9-1) to obtain 23.1 g of the expected product melting at 80° C.

STEP D: Ethyl 1-benzoyl-4-[2-(1H-indol-3-yl)-ethyl]-3-oxo-2-piperazine-acetate 22.4 g of the product of Step C were dissolved in 225 ml of tetrahydrofuran and 14.3 ml of triethylamine and the mixture was cooled to 5° C. 7.9 ml of benzoyl chloride were slowly added and then stirring was maintained for 1 hour at ambient temperature. The insoluble part was separated and the filtrate was evaporated to dryness to obtain 28.4 g of the expected product melting at 144° C.

STEP E: CIS (+) ethyl 2-benzoyl-1,2,3,4,6,7,12,12 b-octahydropyrazono-[1',2'-1,2]-pyrido-[3,4-b]-indole-1-acetate hydrochloride 11.4 g of the product of Step D in 40 ml of phosphorus oxychloride were heated at 90° C. for 2 hours, and after bringing to dryness, the residue was taken up in 50 ml of acetone. The solution was poured slowly over a mixture of 30 ml of 56% hydriodic acid and 300 ml of iced water and stirred at 0° C. for 1 hour. The precipitate was separated, dried and 150 ml of methanol were added while stirring. Then, in small fractions 2.5 g of sodium borohydride were introduced and stirring was maintained for 30 minutes. 10 ml of acetic acid were added, and after stirring for a quarter of an hour, 20 ml of ammonia were added followed by 200 ml of iced water. The precipitate formed was separated, washed with water and dried at 80° C. under reduced pressure. Then, the product was chromatographed on silica (eluent: methylene chloride-ethyl acetate 5-5) to obtain 7.25 g of the expected product in the form of a base melting at 260° C.

Starting from 3.4 g of the base in 100 ml of ethanol and 100 ml of ethyl acetate with 0.69 ml of 11.8N hydrochloric acid, 3 g of the expected hydrochloride were prepared.

| IR Spectrum of the base (CHCL$_3$): | |
|---|---|
| =C—NH— | 3,459 cm$^{-1}$ |
| Associated NH and/or OH | 3,223 and 3,204 cm$^{-1}$ (doublet) |

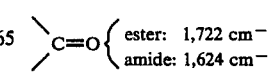

STEP F: (±)
20,21-dinor-17-aza-eburnamenin-14(15H)-one dihydrochloride 19.6 g of the product of Step E in the form of a base in 250 ml of 5N hydrochloric acid were refluxed for 21 hours, treated with active charcoal, filtered and alkalized by the addition of concentrated ammonia. Extraction was carried out with methylene chloride and the extracts were washed with water, dried, concentrated to dryness, and chromatographed on silica (eluent: methylene chloride-methanol 9-1) to obtain 7 g of the expected product in the form of a base melting at 200° C.

3 g of the base were dissolved in 100 ml of ethyl acetate and 100 ml of isopropanol. 1.9 ml of 11.8N hydrochloric acid were added, and after separating, washing with ethyl acetate and with ethanol, 3.52 g of crude product were obtained which was purified by triturating in hot ethanol to obtain 3.2 g of the expected dihydrochloride.

| IR Spectrum (base) (CHCl$_3$): | |
|---|---|
| C=O | 1,704 cm$^{-1}$ |
| C=C | 1,632 cm$^{-1}$ |
| + aromatic | 1,602 cm$^{-1}$ |
|  | 1,473 cm$^{-1}$ |
| NH type | 3,340 cm$^{-1}$ |

EXAMPLE 2
(±) 17-(2-phenylethyl)-17-aza-20,21-dinoreburnamenin-14(15H)-one dihydrochloride 4.37 g of sodium iodide were dissolved at 60° C. in 50 ml of dimethylformamide, and under these conditions 3.9 ml of 2-phenylethyl bromide were added with stirring. After half an hour, 2.6 g of (±) 17-aza-20,21-dinoreburnamenin-14(15H)-one were added and then 4.03 g of potassium carbonate. The mixture was stirred at 60° C. for 72 hours and allowed to return to ambient temperature. 100 ml of water were added, followed by extraction with methylene chloride. The organic phase was washed with water until neutral, dried and brought to dryness. The residue was chromatographed on silica (eluent: methylene chloride-methanol 95-5) to obtain 900 mg of the expected product in the form of a base melting at 200° C.

1.55 g of the base were dissolved in 100 ml of an ethyl acetate-ethanol mixture (1-1) and 0.71 ml of 11.8N hydrochloric acid were added. The mixture was stirred for 4 hours and the precipitate was separated, washed with ethanol and then with ethyl acetate to obtain 1.65 g of the expected product melting at 220° C.

EXAMPLE 3
(±) 17-methyl-17-aza-20,21-dinoreburnamenin-14(15H)-one neutral maleate A mixture of 4.26 g of (±) 20,21-dinor-17-azaeburnamenin-14(15H)-one, 17 ml of 40% formic aldehyde and 11 ml of formic acid was heated at 70° C. for 30 minutes and the reaction mixture was poured over water and ice, alkalized by addition of ammonia and extracted with methylene chloride. The organic phase was washed with water, dried and brought to dryness. The residue was chromatographed on silica (eluent: methylene chloride-methanol 93-7) to obtain 2.55 g of the expected product in the form of a base.

2.1 g of the latter were dissolved in 100 ml of ethyl acetate and 50 ml of ethanol and 867 mg of maleic acid were added, followed by stirring for 3 hours 30 minutes. The precipitate was separated and washed with ethyl acetate and then with ethanol to obtain 2.6 g of the expected product melting at 255° C.

EXAMPLE 4
(±) 17-benzoyl-14,15-dihydro-14-oxo-17-aza-20,21-dinoreburnamenine hydrochloride 2.5 g of (±) 20,21-dinor-17-azaeburnamenin-14(15H)-one were dissolved in 80 ml of tetrahydrofuran and 2 ml of triethylamine, and the mixture was cooled to 10° C. 1.1 ml of benzoyl chloride were slowly added while maintaining the temperature at 10°-15° C. and stirring was carried out for a further hour at ambient temperature. The precipitate was separated and the filtrate was brought to dryness. The residue was triturated with isopropyl ether, then separated, washed with water and dried to obtain 2.62 g of the expected product in the form of a base melting at 210° C. The latter was dissolved in a mixture (1-1) of tetrahydrofuran and ethanol and 0.6 ml of 11.8N hydrochloric acid were added. The mixture was stirred for 1 hour at ambient temperature and the precipitate was separated, washed with ethanol and then with isopropyl ether to obtain 2.61 g of the expected product.

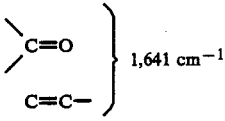

| IR Spectrum | Nujol: |
|---|---|
| C=O region | 1,711 cm$^{-1}$ |
|  | $\left.\begin{array}{c}\text{C=O}\\\text{C=C—}\end{array}\right\}$ 1,641 cm$^{-1}$ |
| aromatic | 1,602 cm$^{-1}$ |
|  | 1,582 cm$^{-1}$ |
|  | 1,494 cm$^{-1}$ |

EXAMPLE 5
(16α) (±) 17-benzoyl-14,15-dihydro-14-oxo-17-aza-20,21-dinoreburnamenine hydrochloride

STEP A:
17-benzoyl-3,16-didehydro-14,15-dihydro-14-oxo-17-aza-20,21-dinoreburnamenine 35 g of ethyl 1-benzoyl-4-[2-(1H-indol-3-yl)-ethyl]-3-oxo-2-piperazine acetate in 60 ml of phosphorus oxychloride were heated at 90° C. for 3 hours and after taking to dryness, the residue was taken up in acetone. The solution was poured over 70 ml of 56% hydroiodic acid in 500 ml of water at 0° C. and stirred for 1 hour. The precipitate was separated and dissolved at 50° C. in 250 ml of acetone. Concentrated ammonia was added at 50° C. over 30 minutes with stirring for 30 minutes at 50° C. 250 ml of water and ice were added to the suspension and the precipitate was separated, washed with water and dried to obtain 24.7 g of the expected product melting at 236° C.

STEP B: (16α) (±) 17 benzoyl-14,15-dihydro-14-oxo-17-aza-20,21-dinoreburnamenine hydrochloride 8.3 g of the product of Step A in 40 ml of acetic acid were stirred while adding in small fractions 4.27 g of sodium borohydride at a temperature at 25° C. and the mixture was stirred at ambient temperature for 30 minutes. After adding 100 ml of iced water and alkalizing with concentrated ammonia, the precipitate was separated, washed with water and dried to obtain 5.2 g of crude product. 3.5 g of the latter were crystallized from dimethyl-formamide to obtain 2.87 g of the expected product in the form of a base which was dissolved in a mixture (1-1) of ethanol and methylene chloride. 0.66 ml of 11.8N hydrochloric acid were added with stirring for 4 hours, and concentration to eliminate the methylene chloride. The precipitate was separated, washed with ethanol and dried to obtain 2.88 g of the expected product.

| IR Spectrum (CHCl$_3$): | |
| --- | --- |
| C=O | 1,708 cm$^{-1}$ |
| C=O and C=C | 1,654 cm$^{-1}$ |
| aromatics | 1,602 cm$^{-1}$ |
|  | 1,580 cm$^{-1}$ |
|  | 1,492 cm$^{-1}$ |

EXAMPLE 6

(16α) (±) 20,21-dinor-17-aza-eburnamenin-14(15H)-one dihydrochloride 5.2 g of (16) (±) 17-benzoyl-14,15-dihydro-14-oxo-17-aza-20,21-dinoreburnamenine in 80 ml of 5N hydrochloric acid were refluxed for 4 and a half hours and the precipitate was separated. The filtrate was alkalized by addition of concentrated ammonia and extraction was carried out with methylene chloride. The organic phase was washed with water to a neutral pH, dried and brought to dryness. The residue was chromatographed on silica (eluent: methylene chloride-methanol 92-8) to obtain 2.4 g of the expected product in the form of a base melting at 190° C. 1.7 g of the base were dissolved in 100 ml of a mixture of ethyl acetate and ethanol (1-1) and 1.08 ml of 11.8N hydrochloric acid were added. The precipitate was separated to obtain 1.86 g of expected product.

| IR Spectrum (CHCl$_3$): | |
| --- | --- |
| C=O | 1,704 cm$^{-1}$ |
| C=C | 1,657 cm$^{-1}$ |
| Bohlmann band | 2,813 cm$^{-1}$ |
| NH | 3,330 cm$^{-1}$ |

EXAMPLE 7

(16α) (±) 17-methyl-17-aza-20,21-dinoreburnamenin-14(15H)-one neutral maleate 2.85 g of (16) (±) 20,21-dinor-17-azaeburnamenin-14(15H) one were dissolved in 30 ml of methylene chloride and 2.95 g of potassium carbonate dissolved in 30 ml of water were added. Then, 300 mg of tetrabutyl ammonium hydrogeno-sulfate were added with strong stirring over 10 minutes. Then 1.3 ml of methyl iodide were introduced and after 8 hours of strong stirring, the organic phase was decanted, washed with water to a neutral pH, dried and brought to dryness. The residue was chromatographed on silica (eluent: methylene chloride-methanol (92-8)) to obtain 2.24 g of the product in the form of a base melting at 148° C.

2.2 g of the latter were dissolved in an ethyl acetate-ethanol mixture (1-1) and 907 mg of maleic acid were added with stirring for 3 hours. After separating, washing and drying, 2.5 g of the expected product melting at 240° C. were obtained.

EXAMPLE 8

(16α) (±) 17-(2-phenylethyl)-17-aza-20,21-dinoreburnamenin-14(15H)-one neutral maleate 2.46 g of sodium iodide were dissolved at 50° C. in 10 ml of dimethylformamide and 2.2 ml of 2-phenylethyl bromide were added. The mixture was stirred at 50° C. for 30 minutes. Under the same conditions, 2.2 g of (16α) (±) 20,21-dinor-17-aza-eburnamenin-14(15H)-one were introduced, then 2.27 g of potassium carbonate, and the same conditions were maintained for 2 hours, then for 72 hours at ambient temperature. The precipitate was separated and dissolved in methylene chloride. The organic phase was dried and brought to dryness and the residue was triturated in 100 ml of pentane. After separating, 2.55 g of the expected product were obtained in the form of a base melting at 141° C.

2.19 g of the base were dissolved in 100 ml of a mixture of ethyl acetate and ethanol (1-1) and 684 mg of maleic acid dissolved in 10 ml of ethanol were added. After 15 hours of stirring, the precipitate was separated to obtain 2.55 g of the expected product melting at 220° C.

EXAMPLE 9

(14α, 16α) (±) 14,15-dihydro-17-aza-20,21-dinoreburnamenin-14-ol 7.1 g of the base of Example 6 were dissolved in 100 ml of tetrahydrofuran and then 17 ml of sodium diethyl-dihydroaluminate were added with stirring for 1 hour at 20° C. After cooling to 0° C., first a mixture of tetrahydrofuran and water (80-20), then 100 ml of water were added slowly with stirring for 2 hours, while allowing it to return to ambient temperature. Extraction was done with methylene chloride and the extracts were dried and concentrated to dryness under reduced pressure. The residue was taken up in 100 ml of N hydrochloric acid with stirring for 15 minutes at ambient temperature, and alkalization with ammonia, followed by filtering and extracting with methylene chloride. The precipitate was filtered, and the filtrate was dried and concentrated under reduced pressure to obtain 6.3 g of crude product which after crystallization from toluene melted at 246° C.

| $C_{16}H_{19}N_3O$: molecular weight = 269.346 | | | |
| --- | --- | --- | --- |
|  | % C | % H | % N |
| Calculated: | 71.35 | 7.11 | 15.6 |
| Found: | 71.6 | 7.3 | 15.6 |

EXAMPLE 10

(16α) (±)
17-(1-methylethyl)-17-aza-20,21-dinoreburnamenin-14(15H)-one (E) 2-butenedioate 2 g of the base of Example 6 were dissolved in 40 ml of tetrahydrofuran and 10 ml of hexamethylphosphotriamide and 5.17 g of potassium carbonate, then 3.7 ml of isoporpyl iodide were added. After stirring for 72 hours at 50° C., the precipitate was separated and the filtrate was concentrated to dryness. The residue was taken up in methylene chloride, washed with water, dried and the solvent was eliminated under reduced pressure. After chromatography on silica (eluent: methylene chloride-methanol 97-3), the residue was triturated in pentane and dried at 60° C. under reduced pressure to obtain 2 g of the expected product in the form of a base, which was dissolved in ethyl acetate. 1.5 g of fumaric acid dissolved in 30 ml of isopropanol were added and stirring was carried out for 15 hours at ambient temperature. The precipitate was separated and dried under reduced pressure at 60° C. to obtain 2.6 g of the expected neutral fumarate melting at 220° C.

| Analysis: $C_{23}H_{27}N_3O_5$; molecular weight = 425.488 | | | |
|---|---|---|---|
| | % C | % H | % N |
| Calculated: | 64.93 | 6.39 | 9.87 |
| Found: | 64.8 | 6.3 | 9.6 |

EXAMPLE 11

(16α) (±)
17-ethyl-17-aza-20,21-dinoreburnamenin-14(15H)-one (Z) 2-butenedioate 0.5 g of the base of Example 6 were dissolved in 10 ml of tetrahydrofuran and 0.52 ml of triethylamine, then 0.3 ml of ethyl iodide were added. After refluxing for 18 hours, the suspension was filtered and the filtrate was concentrated to dryness under reduced pressure. The residue was chromatographed on silica (eluent: methylene chloride-methanol 95-5) to obtain 0.57 g of the expected product in the form of a base melting at 120° C. 2,4 g of base was dissolved in an ethyl acetate-ethanol mixture (1-1) and 0.942 g of maleic acid were added. The mixture was stirred for 2 hours at ambient temperature, then filtered and dried at 60° C. under reduced pressure to obtain 2.44 g of the expected product melting at 183° C.

| Analysis: $C_{18}H_{21}N_3O$, $C_4H_4O_4$: molecular weight = 411.461 | | | |
|---|---|---|---|
| | % C | % H | % N |
| Calculated: | 64.22 | 6.12 | 10.21 |
| Found: | 64.2 | 6.1 | 10.1 |

EXAMPLE 12

(16α) (±)
17-propyl-17-aza-20,21-dinoreburnamenine-14(15H)-one (Z) 2-butenedioate Using the procedure of Example 11, 0.2 g of the base of Example 6, 0.208 ml of triethylamine and 0.145 ml of n-iodopropyl were reacted to obtain 0.32 g of the expected product in the form of a base melting at 127° C.

| Analysis: $C_{19}H_{23}N_3O$, $C_4H_4O_4$; molecular weight = 425.488 | | | |
|---|---|---|---|
| | % C | % H | % N |
| Calculated: | 64.93 | 6.39 | 9.87 |
| Found: | 65.2 | 6.5 | 9.8 |

EXAMPLE 13

(14 α,16α) (±)
14,15-dihydro-17-methyl-17-aza-20,21-dinoreburnmenin-14-ol

Using the procedure of Example 9, 2.81 g of the base of Example 7 and 6 ml of sodium diethyldihydroaluminate and carrying out this reduction at −10° C. were reacted to obtain 2.5 g of crude product which was crystallized from an ethanol-ethyl acetate mixture (6-2) to obtain 1.74 g of the expected product melting at 238° C.

| Analysis: $C_{17}H_{21}N_3O$; molecular weight = 283.376 | | | |
|---|---|---|---|
| | % C | % H | % N |
| Calculated: | 72.0 | 7.5 | 14.5 |
| Found: | 72.0 | 7.5 | 14.7 |

EXAMPLE 14

(16α) (±) 17-methyl-17-aza-20,21-dinoreburnamenine neutral maleate 4.2 g of the product of Example 13 were dissolved in 50 ml of toluene and 80 mg of p-toluene sulfonic acid were added. The mixture was refluxed for 5 hours and after concentrating to dryness, the residue was chromatographed on slica (eluent: methylene chloride-methanol 9-1) to obtain 3.5 g of the expected product in the form of a base melting at 166° C.

1.5 g of the base were dissolved in 100 ml of an ethyl acetate-ethanol mixture (1-1) and 0.656 g of maleic acid were added. After stirring for 3 hours 45 minutes, the precipitate was separated, washed with ethanol, then with ethyl acetate and dried at 60° C. under reduced pressure to obtain 1.61 g of the expected maleate melting at 215° C.

| Analysis: $C_{21}H_{23}N_3O$; molecular weight = 381.435 | | | |
|---|---|---|---|
| | % C | % H | % N |
| Calculated: | 66.13 | 6.08 | 11.0 |
| Found: | 66.0 | 5.9 | 11.0 |

EXAMPLE 15

(16α) (±)
14,15-dihydro-17-methyl-17-aza-20,21-dinoreburnamenine neutral maleate 1.8 g of the base of Example 14 were dissolved in 100 ml of ethanol and 90 mg of platinum oxide were added. The mixture was hydrogenated for 2 and a half hours, then filtered. The filtrate was concentrated to dryness under reduced pressure, and after drying at 60° C. 1.81 g of the expected product were obtained in the form of a base melting at 140° C.

The maleate was prepared as indicated in Example 14 starting with 1.96 g of the base to obtain 2.09 g of maleate melting at 212° C.

| Analysis: $C_{21}H_{25}N_3O_4$; molecular weight = 383.451 | | | |
|---|---|---|---|
| | % C | % H | % N |
| Calculated: | 65.78 | 6.57 | 10.96 |
| Found: | 65.6 | 6.4 | 10.8 |

EXAMPLE 16

(14α, 16α) (±) 17-acetyl-14,15-dihydro-14-hydroxy-17-aza-20,21-dinoreburnamenine 2.5 g of the product of Example 9 in suspension in 30 ml of tetrahydrofuran and 2 ml of triethylamine were cooled to 10° C. and 0.66 ml of acetyl chloride were added slowly and then was stirred for 1 and a half hours. The precipitate was separated, washed with water and dried at 80° C. under reduced pressure to obtain 2.6 g of the expected product melting at 260° C.

EXAMPLE 17

(16α) (±) 17-acetyl-17-aza-20,21-dinoreburnamenine 52 mg of p-toluene sulfonic acid were added to a suspension of 2.6 g of the product of Example 16 in 80 ml of toluene and the mixture was refluxed for 6 hours. The solution was concentrated to dryness under reduced pressure and the residue was washed with water, dried at 80° C. to obtain 2.1 g of the expected product melting at 180° C.

EXAMPLE 18

(16α) (±) 17-aza-20,21-dinoreburnamenine neutral maleate 2.1 g of the product of Example 17 in a mixture of 25 ml of ethanol and 2 ml of potassium hydroxide were heated for 5 hours at reflux and 50 ml of water were added, followed by extraction with methylene chloride. The extracts were washed with water, dried, and concentrated to dryness under reduced pressure. The residue was chromatographed on silica (eluent: methylene chloride-methanol 9-1) to obtain 1.42 g of the expected product melting at 135° C.

The maleate was prepared as in Example 14 starting with 1.4 g of the base to obtain 1.8 g of the expected maleate melting at 246° C.

| Analysis: $C_{20}H_{21}N_3O_4$; molecular weight = 367.408 | | | |
|---|---|---|---|
| | % C | % H | % N |
| Calculated: | 65.38 | 5.76 | 11.44 |
| Found: | 65.2 | 5.7 | 11.4 |

EXAMPLE 19

(14β,16α) (±) 14,15-dihydro-17-(1-methylethyl)-17-aza-20,21-dinoreburnamenin-14-ol Using the procedure of Example 9, 4.5 g of the base of Example 10 and 9.4 ml of sodium diethyldihydroaluminate, carrying out the reduction at −5° C. were reacted to obtain 3.7 g of the expected product melting at 211° C.

EXAMPLE 20

(16α) (±) 17-(1-methylethyl)-17-aza-20,21-dinoreburnamenine

Using the procedure of Example 17, 3.2 g of the product of Example 19 were reacted to obtain 2.8 g of the expected product melting at <50° C.

EXAMPLE 21

(16α) (±) 14,15-dihydro-17-(1-methylethyl)-17-aza-20,21-dinoreburnamenine fumarate Using the procedure of Example 15, 2.8 g of the product of Example 20 were reacted to obtain 2.77 g of the expected product in the form of a base melting at 130° C., then 3.28 g of fumarate melting at 230° C.

| Analysis: $C_{25}H_{31}N_3O_6$; molecular weight = 469.535 | | | |
|---|---|---|---|
| | % C | % H | % N |
| Calculated: | 63.95 | 6.65 | 8.95 |
| Found: | 63.6 | 6.7 | 8.7 |

EXAMPLE 22

(16α) 17-benzoyl-14,15-dihydro-11-methyl-14-oxo-17-aza-20,21-dinoreburnamenine

STEP A:
2-[[2-(6-methyl-1H-indol-3-yl)-ethyl]-amino]-acetonitrile 17 g of 6-methyltryptamine were dissolved at 40° C. under inert atmosphere in 500 ml of tetrahydrofuran, and the solution was allowed to return to ambient temperature. 14.6 ml of 1,5-diaza[5,4,0]undec-5-ene were added followed by 6.2 ml of chloroacetonitrile and stirring for 15 hours. The solvent was eliminated under reduced pressure and the residue was taken up in 250 ml of methylene chloride, washed with water, dried and concentrated to dryness. The 25 g of crude product was purified by chromatography on silica (eluent: methylene chloride-ethyl acetate 3-7) to obtain 13.2 g of the expected product melting at 92° C.

STEP B:
1-[2-(6-methyl-1H-indol-3-yl)-ethyl]-ethanediamine hydrochloride

Using the procedure of Step B of Example 1, 13.2 g of the product of Step A were reacted to obtain 13.4 g of the base. 0.170 g of the base were dissolved in 1 ml of isopropanol and 0.13 ml of concentrated hydrochloric acid was added at 0° C. After stirring for 20 minutes, the precipitate was filtered, washed with isopropyl ether and dried to obtain 0.170 g of the expected hydrochloride melting at >260° C.

STEP C: Ethyl 4-[2-(6-methyl-1H-indol-3-yl)-ethyl]-3-oxo-2-piperazine acetate Using the procedure of Step C of Example 1, 13 g of the base of Step B and 16.4 ml of ethyl maleate were reacted to obtain 10 g of the expected product.

STEP D: Ethyl 1-benzoyl-4-[2-(6-methyl-1H-indol-3-yl)-ethyl]-3-oxo-2-piperazine acetate Using the procedure of Step D of Example 1, 10 g of the product of Step C and 3.36 ml of benzoyl chloride were reacted to obtain 13 g of expected product melting at 155° C.

STEP E: 17-benzoyl-3,16-didehydro-14,15-dihydro-11-methyl-14-oxo-17-aza-20,21-dinoreburnamenine 11.6 g of the product of Step D were heated for 3 hours at 75° C. in 23.5 ml of phosphorus oxychloride and then allowed to return to ambient temperature. The mixture was poured over an iced aqueous solution of perchloric acid and after stirring for 1 hour at 0° C., the precipitate was filtered off, taken up in acetone and heated to 50° C. 120 ml of concentrated ammonia were added over 30 minutes and the mixture was stirred for 75 minutes at 50° C. The resulting mixture was allowed to return to ambient temperature, and was poured into iced water. The precipitate was filtered off, washed with water and dried at 50° C. under reduced pressure to obtain 8.2 g of the expected product melting at 250° C.

STEP F: (16α) 17-benzoyl-14,15-dihydro-11-methyl-14-oxo-17-aza-20,21-dinoreburnamenine 8.2 g of the product of Step E were stirred in 85 ml of acetic acid and in small fractions, 4.6 g of sodium borohydride were added at a temperature of less than 50° C. After stirring for 1 hour at ambient temperature, the acetic acid was eliminated and the remainder was alkalized with concentrated ammonia, followed by stirring for 15 minutes. The precipitate was filtered off, washed with water and dried at 70° C. to obtain 5.93 g of the expected product melting at 262° C.

| IR Spectrum (CHCl$_3$): | |
|---|---|
| —C=O: | 1,717 cm$^{-1}$, 1,700 cm$^{-1}$ |
| C=C: | 1,653 cm$^{-1}$ |
| Conjugated and aromatic system | 1,638 cm$^{-1}$, 1,616 cm$^{-1}$, 1,576 cm$^{-1}$ |

EXAMPLE 23

(16α) (±)
11-methyl-17-aza-20,21-dinoreburamenin-14(15H)-one 5.9 g of the product of Example 22 were refluxed for 6 hours in 72 ml of 5N hydrochloric acid and the precipitate was eliminated by filtration. The filtrate was alkalized with an aqueous solution of sodium hydroxide, followed by extraction with methylene chloride. The organic phase was washed with water, dried and concentrated to dryness under reduced pressure. The residue was chromatographed on silica (eluent: methylene chloride-methanol 96-4) to obtain 3.1 g of the expected product melting at 196° C.

| IR Spectrum (CHCl$_3$): | |
|---|---|
| NH: | 3,470 cm$^{-1}$ |
| —C=O | 1,702 cm$^{-1}$ |
| —C=C—: | 1,659 cm$^{-1}$ |
| Aromatic: | 1,612 cm$^{-1}$, 1,600 cm$^{-1}$ |

EXAMPLE 24

(16α) (±)
11,17-dimethyl-17-aza-20,21-dinoreburnamenin-14(15H)-one neutral maleate Using the procedure of Example 7, 3.1 g of the product of Example 23, 3.05 g of potassium carbonate, 1.4 ml of methyl iodide and 0.3 g of tetrabutylammonium hydrogenosulfate were reacted to obtain 2.1 g of the expected product in the form of a base melting at 171° C. and then 2.07 g of the expected maleate melting at 215° C.

| Analysis: $C_{18}H_{21}N_3O$, $C_4H_4O_4$: molecular weight = 411,467 | | | |
|---|---|---|---|
| | % C | % H | % N |
| Calculated: | 64.22 | 6.12 | 10.21 |
| Found: | 64.2 | 6 | 10.1 |

EXAMPLE 25

(16α) (±)
14,15-dihydro-11-methoxy-14-oxo-17-aza-20,21-dinoreburnamenine

STEP A: 2-[[2-(6-methoxy-1H-indol-3-yl)-ethyl]-amino]-acetonitrile 28.5 g of 6-methoxytryptamine were refluxed in 300 ml of tetrahydrofuran in the presence of 42 ml of triethylamine and 11.4 ml of chloroacetonitrile were added over 2 hours. The heating was continued for 1 hour and after allowing the temperature to return to the ambient, the precipitate was eliminated by filtration. The filtrate was concentrated to dryness under reduced pressure and the residue was taken up in ethyl acetate, washed with water, dried and the solvent was eliminated under reduced pressure to obtain 17.9 g of the expected product melting at approx. 80° C.

STEP B: 1-[2-(6-methoxy-1H-indol-3-yl)-ethyl]-ethanediamine hydrochloride

Using the procedure of Step B of Example 1, 17.9 g of the product of Step A were reacted to obtain 17.2 g of the expected product. 0.58 g of the base were dissolved in 20 ml of ethyl acetate and 30 ml of ethanol and then 0.42 ml of hydrochloric acid were added at 0° C. followed by stirring 1 hour at 20° C. The precipitate was separated and dried to 20° C. under reduced pressure to obtain 0.440 g of the expected hydrochloride melting at 200° C.

STEP C: Ethyl 4-[2-(6-methoxy-1H-indol-3-yl)-ethyl]-3-oxo-2-piperazine acetate Using the procedure of Step C of Example 1, 17.2 g of the base of Step B and 17.9 ml of diethyl maleate were reacted to obtain 14 g of the expected product.

STEP D: Ethyl 1-benzoyl-4-[2-(6-methoxy-1H-indol-3-yl)-ethyl]-3-oxo-2-piperazine acetate Using the procedure of Step D of Example 1, 14 g of the product of Step C, 8.2 ml of triethylamine and 4.5 ml of benzoyl chloride were reacted to obtain 18 g of the expected product.

STEP E: 17-benzoyl-3,16-didehydro-14,15-dihydro-11-methoxy-14-oxo-17-aza-20,21-dinoreburnamenine Using the procedure of Step E of Example 22, 18 g of the product of Step D, 36 ml of phosphorus oxychloride, 18 ml of perchloric acid and 180 ml of concentrated ammonia were reacted to obtain 12 g of the expected product melting at 220° C.

STEP F: (16α) (±) 14,15-dihydro-11-methoxy-14-oxo-17-aza-20,21-dinoreburnamenine Using the procedure of Step F of Example 22, 12 g of the product of Step E, 5.8 g of sodium borohydride and 300 ml of acetic acid were reacted to obtain 10 g of the expected product melting at >260° C.

| IR Spectrum (CHCl$_3$): | |
|---|---|
| $\diagdown$ C=O $\diagup$ | 1,705 cm$^{-1}$, 1,650 cm$^{-1}$ |
| C=C + aromatic | 1,656 cm$^{-1}$, 1,615 cm$^{-1}$, 1,602 cm$^{-1}$, 1,580 cm$^{-1}$, 1,488 cm$^{-1}$ |

EXAMPLE 26

(16α) (±) 11-methoxy-17-aza-20,21-dinoreburnamin-14(15H)

Using the procedure of Example 23, 10 g of the product of Example 25 and 200 ml of 5N hydrochloric acid were reacted to obtain 4.64 g of the expected product melting at 142° C.

| IR Spectrum (CHCl$_3$): | |
|---|---|
| —C=O | 1,704 cm$^{-1}$ |
| C=C— + aromatic | 1,661 cm$^{-1}$, 1615 cm$^{-1}$, 1,578 cm$^{-1}$, 1,487 cm$^{-1}$ |
| NH | 3,330 cm$^{-1}$ |

EXAMPLE 27

(16α) (±) 11-methoxy-17-methyl-17-aza-20,21-dinoeburnamenin-14 (15H)-one neutral maleate Using the procedure of Example 7, 2.5 g of the product of Example 26, 2.32 g of potassium carbonate, 1.05 ml of methyl iodide and 0.25 g of tetrabutylammonium hydrogensulfate were reacted to obtain 1.5 g of the expected product in the form of a base melting at 143° C. and then 1.57 g of the expected maleate melting at 210° C.

| Analysis: C$_{22}$H$_{25}$N$_3$O$_6$: molecular weight = 427.46 | | | |
|---|---|---|---|
| | % C | % H | % N |
| Calculated: | 61.82 | 5.89 | 9.83 |
| Found: | 61.6 | 5.9 | 9.8 |

EXAMPLE 28

(16α) (±) 17-benzoyl-14,15-dihydro-10-methoxy-14-oxo-17-aza-20,21-dinoreburnamenine

STEP A: 2-[[2-(5-methoxy-1H-indol-3-yl)-ethyl]-amino]-acetonitrile

Using the procedure of Step A of Example 25, 25 g of 5-methoxytryptamine, 10 ml of chloroacetonitrile and 37 ml of triethylamine were reacted to obtain 20.9 g of the expected product.

STEP B: 1-[2-(5-methoxy-1H-indol-3-yl)-ethyl]-ethanediamine

Using the procedure of Step B of Example 1, 2 g of the product of Step A were reacted to obtain 2.02 g of the expected product.

STEP C: Ethyl 4-[2-(5-methoxy-1H-indol-3-yl)-ethyl]-3-oxo-2-piperazine acetate Using the procedure of Step C of Example 1, 21.4 g of the product of Step B and 22.3 ml of diethyl maleate were reacted to obtain 13.9 g of the expected product.

STEP D: Ethyl 1-benzoyl-4-[2-(5-methoxy-1H-indol-3-yl)-ethyl]-3-oxo-2-piperazine acetate Using the procedure of Step D of Example 1, 13.9 g of the product of Step C, 8.2 ml of triethylamine and 4.5 ml of benzoyl chloride were reacted to obtain 18 g of the expected product.

STEP E: 17-benzoyl-3,16-didehydro-14,15-dihydro-10-methoxy-14-oxo-17-aza-20,21-dinoreburnamenine Using the procedure of Step E of Example 22, 18 g of the product of Step D, 36 ml of phosphorus oxychloride, 36 ml of perchloric acid and 180 ml of concentrated ammonia were reacted to obtain 11 g of the expected product melting at 243° C.

STEP F: (16α) (±) 17-benzoyl-14,15-dihydro-10-methoxy-14-oxo-17-aza-20,21-dinoreburnamenine Using the procedure of Step F of Example 22, 11 g of the product of Step E, 5.3 g of sodium borohydride and 250 ml of acetic acid were reacted to obtain 8.7 g of the expected product melting at approx. 260° C.

| IR Spectrum (Nujol): | |
|---|---|
| —C=O: | 1,699 cm$^{-1}$ |

-continued

IR Spectrum (Nujol):

$-\underset{\underset{O}{\|}}{C}=C-N\genfrac{}{}{0pt}{}{\diagup}{\diagdown}\genfrac{}{}{0pt}{}{\text{doublet}}{\text{approx}}$  1,650 cm$^{-1}$ aromatic  1,609 cm$^{-1}$, 1,600 cm$^{-1}$, 1,580 cm$^{-1}$

EXAMPLE 29

(16α) (±)
10-methoxy-17-aza-20,21-dinoreburnamenin-14(15H)-one

Using the procedure of Example 23, 7.1 g of the product of Example 28 and 250 ml of 5N hydrochloric acid were reacted to obtain 3.74 g of the expected product melting at 209° C.

IR Spectrum (CHCl$_3$):

—C=O:  1,701 cm$^{-1}$
—C=C—  
+ aromatic  } 1,656 cm$^{-1}$, 1,624 cm$^{-1}$, 1,614 cm$^{-1}$, 1,580 cm$^{-1}$
NH:  3,320 cm$^{-1}$

EXAMPLE 30

(16α) (±)
10-methoxy-17-methyl-17-aza-20,21-dinoreburnamenine neutral maleate 2 g of the product of Example 29 were dissolved in a mixture of 3.8 ml of triethylamine and 100 ml of tetrahydrofuran and at 60° C., 1.7 ml of methyl iodide were added over 4 hours. The mixture was refluxed for 30 minutes, allowed to return to ambient temperature and the precipitate was filtered off. The filtrate was concentrated to dryness and the residue was purified by chromatography on silica (eluent: methylene chloride-methanol 95-5) and after drying at 50° C. under reduced pressure, 1.4 g of the expected product melting at 173° C. were obtained 1.86 g of the said base were dissolved in 100 ml of ethyl acetate an 4.693 g of maleic acid dissolved in 100 ml of boiling ethyl acetate were added and the mixture was stirred for 5 hours at ambient temperature. After separating, washing with ethyl acetate and drying at 70° C. under reduced pressure, 2.34 g of the expected neutral maleate melting at 192° C. were obtained.

Analysis: C$_{18}$H$_{21}$N$_3$O$_2$, C$_4$H$_4$O$_4$; molecular weight = 427,46

|  | % C | % H | % N |
|---|---|---|---|
| Calculated: | 61.82 | 5.89 | 9.83 |
| Found: | 61.5 | 5.9 | 9.6 |

EXAMPLE 31

17-dodecanoyl-3,16-didehydro-14,15-dihydro-14-oxo-17-aza-20,21-dinoreburnamenine STEP A: Ethyl 4-[2-(1H-indol-3-yl)-ethyl]-3-oxo-1-(1-oxododecyl)-2-piperazine acetate 2.14 g of the product of Step C of Example 1 were dissolved in a mixture containing 1.4 ml of triethylamine and 25 ml of tetrahydrofuran. 1.5 ml of lauryl chloride were added dropwise and after stirring for 30 minutes, the precipitate was filtered off. The filtrate was concentrated to dryness and the residue was taken up in methylene chloride, washed with water and dried. The solvent was eliminated under reduced pressure at 50° C. to obtain 3.2 g of the expected product.

STEP B:
17-dodecanoyl-3,16-didehydro-14,15-dihydro-14-oxo-17-aza-20,21-dinoreburnamenine 6.4 g of the product of Step A were dissolved in 25 ml of phosphorus oxychloride and heated for 1 hour 90° C. After concentrating to dryness, the residue was taken up in 50 ml of acetone, heated to 55° C., and over 30 minutes, 60 ml of concentrated ammonia were added. After stirring for 1 hour, the mixture was poured into iced water and stirred for 1 hour at 0° C. The precipitate was separated, washed with water, triturated in acetone and dried at 50° C. under reduced pressure to obtain 1.9 g of crude product which was taken up in methylene chloride. The solution was filtered on silica and the filtrate was concentrated to dryness. The residue was taken up in methanol and dried under reduced pressure at 50° C. to obtain 1.2 g of the expected product melting at 146° C.

Analysis: C$_{26}$H$_{37}$N$_3$O$_2$; molecular weigt = 447.626

|  | % C | % H | % N |
|---|---|---|---|
| Calculated: | 75.13 | 8.33 | 9.39 |
| Found: | 75 | 8.4 | 9.2 |

EXAMPLE 32

(16α) (±)
17-benzoyl-14,15-dihydro-10-chloro-14-oxo-17-aza-20,21-dinoreburnamenine STEP A:
2-[[2-(5-chloro-1H-indol-3-yl)-ethyl]-amino]-acetonitrile Using the procedure of Step A of Example 22, 21.4 g of 5-chlorotryptamine, 7.7 ml of chloroacetonitrile and 18.1 ml of 1,5-diaza[5,4,0]undec-5-ene in 210 ml of tetrahydrofuran were reacted to obtain 19.3 g of the expected product melting at 80° C.

STEP B:
1-[2-(5-chloro-1H-indol-3-yl)-ethyl]-ethanediamine dihydrochloride

Using the procedure of Step B of Example 1, 0.5 g of the product of Step A were reacted to obtain 0.43 g of product in the form of a base which was converted into 0.400 g of its dihydrochloride by the action of 0.3 ml of 11.8N hydrochloric acid melting at 220° C.

STEP C: Ethyl
4-[2-(5-chloro-1H-indol-3-yl)-ethyl]-3-oxo-2-piperazine acetate

Using the procedure of Step C of Example 1, 18.8 g of the base of Step B and 19 ml of diethyl maleate were reacted to obtain 11.03 g of the expected product melting at 136° C.

23

STEP D: Ethyl 1-benzoyl-4-[2-(5-chloro-1H-indol-3-yl)-ethyl]-3-oxo-2-piperazine acetate Using the procedure of Step D of Example 1, 11 g of the product of Step C and 3.5 ml of benzoyl chloride were reacted to obtain 13 g of the expected product.

STEP E: 17-benzoyl-10-chloro-3,16-didehydro-14,15-dihydro-14-oxo-17-aza-20,21-dinoreburnamenine Using the procedure of Step E of Example 22, 7.1 g of the product of Step D, 11 ml of phosphorus oxychloride, 14 ml of perchloric acid and 70 ml of concentrated ammonia were reacted to obtain a crude product which was used as is for the following step.

STEP F: (16α) (±) 17-benzoyl-14,15-dihydro-10-chloro-14-oxo-17-aza-20,21-dinoreburnamenine Using the procedure of Step F of Example 22, the product of Step E, 2.88 g of sodium borohydride and 150 ml of acetic acid were reacted to obtain 0.8 g of expected product melting at >260° C.

| IR Spectrum (CHCl₃): | |
|---|---|
| —C=O: | 1,711 cm⁻¹, 1,652 cm⁻¹ |
| aromatic: | 1,602 cm⁻¹, 1,575 cm⁻¹, 1,569 cm⁻¹ |

EXAMPLE 33

(16α) (±) 10-chloro-17-aza-20,21-dinoreburnamenin-14(15H)-one

Using the procedure of Example 23, 0.8 g of the product of Example 32 and 50 ml of 5N hydrochloric acid were reacted to obtain 0.5 g of the expected product melting at 200° C.

| IR Spectrum (CHCl₃) | |
|---|---|
| —C=O: | 1,710 cm⁻¹ |
| C=C C=N | 1,657 cm⁻¹ |
| + aromatic | 1,602 cm⁻¹, 1,574 cm⁻¹, 1,565 cm⁻¹ |

EXAMPLE 34

(16α) (±) 10-chloro-17-methyl-17-aza-20,21-dinoreburnamenin-14(15H)-one neutral maleate Using the procedure of Example 7, 0.5 g of the product of Example 33, 0.45 g of potassium carbonate, 0.2 ml of methyl iodide and 0.05 g of tetrabutylammonium hydrogenosulfate were reacted to obtain 0.24 g of expected product in the form of a base melting at 211° C. and then 0.195 g of the expected maleate melting at 214° C.

| Analysis: C₂₁H₂₂N₃ClO₅: molecular weight = 431.879 | | | | |
|---|---|---|---|---|
| | % C | % H | % N | % Cl |
| Calculated: | 58.4 | 5.13 | 9.73 | 8.21 |
| Found: | 58.4 | 5.1 | 9.7 | 8.1 |

EXAMPLE 35

Tablets were prepared containing 50 mg of the product of Example 7 and sufficient excipient of lactose, talc, starch and magnesium stearate for a tablet weight of 350 mg.

PHARMACOLOGICAL DATA

Analgesic activity: Hot plate test:

Female mice weighing 22 to 24 g were placed individually on a copper plate maintained at 56° C. and reaction to pain was shown by the animal licking its front paws. The time of this reaction was noted and only those mice reacting in less than 8 seconds were retained. The animals were divided into homogeneous groups and treated with the product under study administered orally with one group receiving only the vehicle. The time of reaction to the pain was again measured 30 to 60 minutes after the treatment. The active dose or AD₁₀₀ was the dose which increased the reaction time by 100% 30 minutes after the treatment, taking into account the variations of reaction time of the control animals. The results are in the following Table.

| Product of Example | AD₁₀₀ in mg/kg |
|---|---|
| 6 | 100 |
| 7 | 100 |
| 12 | ≦100 |
| 15 | 75 |
| 18 | 100 |

Various modifications of the compounds and methods of the invention may be made without departing from the spirit or scope thereof and it is to be understood that the invention is intended to be limited only as defined in the appended claims.

What we claim is:

1. A compound selected from the group consisting of all possible isomeric forms, optically active isomers and racemic mixtures of compounds of the formula

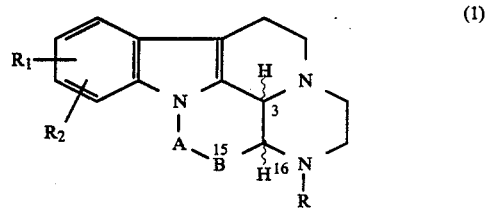

(1)

wherein R₁ and R₂ are individually selected from the group consisting of hydrogen, halogen, alkyl and alkoxy of 1 to 5 carbon atoms, —OH, —CF₃ and —NO₂, R is selected from the group consisting of hydrogen, alkyl of 1 to 5 carbon atoms, aralkyl of 7 to 12 carbon atoms, benzoyl and acyl of an alkanoic acid of 1 to 12 alkyl carbon atoms and

is selected from the group consisting of

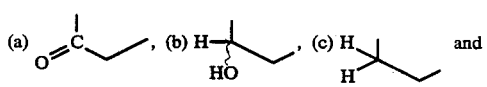

(d) 

and their non-toxic, pharmaceutically acceptable acid addition salts.

2. A compound of claim 1 wherein $R_1$ and $R_2$ are individually selected from the group consisting of hydrogen, methyl, ethyl, methoxy, ethoxy, chlorine, hydroxy, —$CF_3$ and —$NO_2$ and R is selected from the group consisting of hydrogen, methyl, ethyl, propyl, benzyl, phenethyl and benzoyl.

3. A compound of claim 1 wherein $R_2$ is hydrogen and $R_1$ is selected from the group consisting of hydrogen, methoxy, ethoxy and chlorine.

4. A compound of claim 1 wherein the hydrogen atoms in the 3- and 16-positions are trans.

5. A compound of claim 1 selected from the group consisting of (16α) (±) 17-methyl-17-aza-20,21-dinoreburnamenin-14(15H)-one, (16α) (±) 17-propyl-17-aza-20,21dinoreburnamein-14(15H)-one, (16α) (±) 17-aza-20,21-dinoreburnamenine, (16α) (±) 14,15-dihydro-17-methyl-17-aza-20,21-dinoreburnamenine and their non-toxic, pharmaceutically acceptable acid addition salts.

6. An analgesic composition comprising an analgesically effective amount of at least one compound of claim 1 and a pharmaceutical carrier.

7. A composition of claim 6 wherein in the compound $R_1$ and $R_2$ are individually selected from the group consisting of hydrogen, methyl, ethyl, methoxy, ethoxy, chlorine, hydroxy, —$CF_3$ and —$NO_2$ and R is selected from the group consisting of hydrogen, methyl, ethyl, propyl, benzyl, phenethyl and benzoyl.

8. A composition of claim 6 wherein in the compound $R_2$ is hydrogen ans $R_1$ is selected from the group consisting of hydrogen, methoxy, ethoxy and chlorine.

9. A composition of claim 6 wherein in the compound the hydrogen atoms in the 3- and 16-positions are trans.

10. A composition of claim 6 wherein the active compound is selected from the group consisting of (16α) (±) 17-methyl-17-aza-20,21-dinoreburnamenin-14(15H)-one, (16α) (±) 17-propyl-17-aza-20,21-dinoreburnamenin-14(15H)-one, (16α) (±) 17-aza-20,21-dinoreburnamenine, (16α) (±) 14,15-dihydro-17-methyl-17-aza-20,21-dinoreburnamenine and their non-toxic, pharmaceutically acceptable acid addition salts.

11. The method of relieving pain in warm-blooded animals comprising administering to warm-blooded animals an analgesically effective amount of at least one compound of claim 1.

12. A method of claim 11 wherein in the compound $R_1$ and $R_2$ are individually selected from the group consisting of hydrogen, methyl, ethyl, methoxy, ethoxy, chlorine, hydroxy, —$CF_3$ and —$NO_2$ and R is selected from the group consisting of hydrogen, methyl, ethyl, propyl, benzyl, phenethyl and benzoyl.

13. A method of claim 11 wherein in the compound $R_2$ is hydrogen and $R_1$ is selected from the group consisting of hydrogen, methoxy, ethoxy and chlorine.

14. A method of claim 11 wherein in the compound the hydrogen atoms in the 3- or 16-positions are trans.

15. A method of claim 11 wherein the active compound is selected from the group consisting of (16α) (±) 17-methyl-17-aza-20,21-dinoreburnamenin-14(15H)-one, (16α) (±) 17-propyl-17-aza-20,21-dinoreburnamenin-14(15H)-one (16α) (±) 17-aza-20,21-dinoreburnamenine, (16α) (±) 14,15-dihydro-17-methyl-17-aza-20,21-dinoreburnamenine and their non-toxic, pharmaceutically acceptable acid addition salts.

* * * * *